(12) United States Patent
Chenevier

(10) Patent No.: US 8,841,465 B2
(45) Date of Patent: Sep. 23, 2014

(54) METHOD FOR SELECTIVE FUNCTIONALIZATION OF SINGLE-WALLED CARBON NANOTUBES

(75) Inventor: Pascale Chenevier, Villebon sur Yvette (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/124,759

(22) PCT Filed: Jun. 7, 2012

(86) PCT No.: PCT/IB2012/052884
§ 371 (c)(1),
(2), (4) Date: Dec. 11, 2013

(87) PCT Pub. No.: WO2012/168899
PCT Pub. Date: Dec. 13, 2012

(65) Prior Publication Data
US 2014/0114079 A1  Apr. 24, 2014

(30) Foreign Application Priority Data
Jun. 10, 2011 (FR) .................................. 11 55137

(51) Int. Cl.
*C07D 307/62* (2006.01)
*C01B 31/02* (2006.01)

(52) U.S. Cl.
CPC ......... *C01B 31/0273* (2013.01); *C01B 31/0266* (2013.01); *C07D 307/62* (2013.01); *C01B 2202/02* (2013.01)
USPC ....................................................... 549/315

(58) Field of Classification Search
CPC ..................................................... C01B 31/02
USPC ....................................................... 549/315
See application file for complete search history.

(56) References Cited

U.S. PATENT DOCUMENTS

2012/0114549 A1  5/2012  Chenevier

FOREIGN PATENT DOCUMENTS

| JP | 2007 031238 A | 2/2007 |
| JP | 2010 010162 A | 1/2010 |
| WO | WO 2008/057070 A2 | 5/2008 |
| WO | WO 2010/089395 A2 | 8/2010 |

OTHER PUBLICATIONS

Schmidt et al. Chem. Eur. Journal 2011, 17, 1415-1418.*
Darchy et al. C A R B O N, 66, ( 2 0 1 4 ), 2 4 6-2 5 8.*
International Search Report and Written Opinion for Application No. PCT/IB2012/052884 dated Aug. 13, 2012.
Arnold, M.S. et al., *Sorting Carbon Nanotubes by Electronic Structure Using Density Differentiation*, Nature Nanotechnology, vol. 1 (Oct. 2006) 60-65.
Dyke, C. A. et al., *Separation of Single-Walled Carbon Nanotubes on Silica Gel. Materials Morphology and Raman Excitation Wavelength Affect Data Interpretation*, J. Am. Chem. Soc., vol. 127, No. 12 (Mar. 2005) 4497-4509.
Schmidt, G. et al., *Labile Diazo Chemistry for Efficient Silencing of Metallic Carbon Nanotubes*, Chem. Eur. J., vol. 17, No. 5 (Feb. 2011) 1415-1418.
Doyle, CD. et al., Journal of the American Chemical Society 130 (2008) 6795-6800.
Nair, N. et al., Journal of the American Chemical Society 129 (2007) 3946-3954.
Wang, CJ. et al., Journal of the American Chemical Society 127 (2005) 11460-11468.
Ghosh, S. et al., Nano Research 2 (2009) 183-191.
Lee, CW. et al., Advaned Materials 22 (2010) 1278.
Zhang, L. et al., Journal of the American Chemical Society 130 (2008) 2686-2691.
Cabana, J. et al., Journal of the American Chemical Society 129 (2007) 2244.
Tanaka, T. et al., Nano Letters 9 (2009) 1497-1500.
Moshammer, K. et al., Nano Research (2009) 599-606.
Jost, O. et al., Applied Physics Letters 75 (1999) 2217.
Zollinger, H., VCH (1994) 108-115.
Doyle, MP. et al., Journal of Organic Chemistry 54 (1989) 3785-3789.
Dyke, C. A. et al., Synlett 1 (2004) 155-160.

* cited by examiner

*Primary Examiner* — Nizal Chandrakumar
(74) *Attorney, Agent, or Firm* — Alston & Bird LLP

(57) ABSTRACT

The present invention relates to a method for selective functionalization of metallic single-walled carbon nanotubes with a diazonium derivative. The present invention also relates to the use of the mixture of metallic single-walled carbon nanotubes selectively functionalized and to the semiconducting single-walled carbon nanotubes obtained by means of the method according to the invention, for producing transistor channels in particular in electronics, electron acceptor materials, in particular in photovoltaic systems, nonlinear infrared photon emitters or absorbers, current-conducting electrodes, flexible transparent electrodes, antistatic coatings, chemical detectors, and solar cells.

17 Claims, 4 Drawing Sheets

SWNTs Carbon Solutions

SWNTs NanoLedge

METHOD FOR SELECTIVE FUNCTIONALIZATION OF SINGLE-WALLED CARBON NANOTUBES

FIELD

The present invention relates to a process for the selective functionalization of metallic single-walled carbon nanotubes with a diazonium derivative.

The present invention also relates to the use of a mixture of selectively functionalized metallic single-walled carbon nanotubes and of semiconducting single-walled carbon nanotubes obtained by the process according to the invention for the preparation of transistor channels, in particular in electronics, of electron-accepting materials, in particular in photovoltaics, of nonlinear infrared photon emitters or absorbers, of current-conducting electrodes, of flexible transparent electrodes, of antistatic coatings, of chemical detectors or of solar cells.

BACKGROUND

An additional subject matter of the invention is a process for preparing transistor channels, in particular in electronics, electron-accepting materials, in particular in photovoltaics, nonlinear infrared photon emitters or absorbers, current-conducting electrodes, flexible transparent electrodes, antistatic coatings, chemical detectors or solar cells, characterized in that it employs the process for the selective functionalization of metallic single-walled carbon nanotubes according to the invention.

Carbon nanotubes are a promising material simultaneously for their mechanical, electronic and optical qualities. While industrial uses are beginning to see the light in the field of mechanical reinforcing by multi-walled carbon nanotubes (MWNTs), applications in electronics and in optics are slower to arrive. This is because, in these fields, it is the single-walled carbon nanotubes (SWNTs) which show the most novel and the most effective properties.

Unfortunately, single-walled carbon nanotubes (SWNTs) can, depending on the chirality, that is to say the geometry of the winding of the carbon plane, either be metallic (m-SWNTs) or semiconducting (sc-SWNTs). Whatever the method of synthesis, metallic SWNTs and semiconducting SWNTs are generally synthesized in the form of a mixture of the two types.

Metallic and semiconducting SWNTs are both advantageous but for different applications. When metallic and semiconducting SWNTs are in a mixture, the presence of one type is often detrimental to the use of the other.

For example, semiconducting SWNTs can be used as transistor channels, in particular in electronics, or as electron-accepting materials, in particular in photovoltaics; the presence of metallic SWNTs among the semiconducting SWNTs then brings about short circuits. The semiconducting SWNTs can also be used as nonlinear infrared photon emitters in photonics; the metallic SWNTs in contact with the semiconducting SWNTs bring about the extinction of the luminescence.

In the same way, metallic SWNTs can, for example, be used as materials for current-conducting wires, vias or electrodes; the semiconducting SWNTs present among the metallic SWNTs bring about high instability of the conductivity.

The separation of the metallic SWNTs from the semiconducting SWNTs is thus a high requirement identified from the time of their discovery and constitutes the main blocking point for their industrial use. The separation of metallic SWNTs from semiconducting SWNTs has thus become, since the 2000s, a highly competitive and particularly active subject.

Various methods for differentiating, enriching or separating the SWNTs have already been described in the literature.

One of these methods consists in carrying out the selective coupling of the metallic SWNTs with diazonium (Strano M S. et al., Science, 2003, 301, pp. 1519-1522) with the aim of separating the semiconducting SWNTs from the metallic SWNTs (Dyke C A. et al., Journal of the American Chemical Society, 2005, 127, pp. 4497-4509). As the selectivity of this reaction is low, it does not make it possible to obtain either good separation of the starting material or a starting material of good quality. This is because the selective chemical differentiation of the metallic SWNTs is difficult given that the reactivity of the SWNTs does not depend only on the electronic type of the SWNTs but also in large part on their diameter. Thus, the semiconducting SWNTs having a small diameter (diameter generally of less than 1.1 nm) thus have a tendency to react in the same way as the metallic SWNTs having a large diameter (diameter generally of greater than 1.1 nm), thus making it difficult to separate them.

Other teams have also used the reaction of diazoniums with SWNTs to differentiate and separate metallic SWNTs from semiconducting SWNTs. However, the selectivity of the reaction is rarely given by the authors and it is not always possible to determine it from the published data. In the reactions indicated below, the selectivity was roughly estimated from the published tables and spectra.

The group of J. Tour is a pioneer in the reaction of diazoniums with SWNTs. The studies relate to HiPco® SWNTs, which are SWNTs having small diameters, that is to say a diameter of less than or equal to 1.1 nm, in particular a diameter of between 0.9 and 1.1 nm, which are dissolved in aqueous solutions of SDS (sodium lauryl sulfate or sodium dodecyl sulfate). From the published tables and spectra, the selectivity with regard to metallic SWNTs can be estimated at approximately 7 (Doyle C D. et al., Journal of the American Chemical Society, 2008, 130, pp. 6795-6800). In other words, the speed of reaction of the metallic SWNTs is 7 times greater than the speed of reaction of the semiconducting SWNTs.

The group of M. Strano has been working on this reaction for 8 years. All the studies relate to HiPco® SWNTs dissolved in an aqueous solution of SDS, an anionic surfactant, sometimes compared with a neutral surfactant, such as Triton. The selectivity with regard to metallic SWNTs can be estimated at approximately 6 in the best cases, that is to say that the speed of reaction of the metallic SWNTs is approximately 6 times greater than the speed of reaction of the semiconducting SWNTs (Nair N. et al., Journal of the American Chemical Society, 2007, 129, pp. 3946-3954).

Wang and Shim have published a study on the selective functionalization of metallic SWNTs by diazoniums by CVD (chemical vapor deposition). The reactivity of individual SWNTs is measured and compared. The selectivity can be estimated at approximately 5, that is to say that the speed of reaction of the metallic SWNTs is 5 times greater than the speed of reaction of the semiconducting SWNTs (Wang C J. et al., Journal of the American Chemical Society, 2005, 127, pp. 11460-11468).

Ghosh and Rao have used the reaction of diazoniums with SWNTs for a separation of metallic SWNTs from semiconducting SWNTs. They are SWNTs obtained by electric arc (having a large diameter, that is to say a diameter of greater than 1.1 nm, in particular a diameter of between 1.2 and 2 nm, limits included) dissolved in SDS. The selectivity is not accessible. The differentiated SWNTs are separated by ultracentrifuging over a density gradient. The nanotubes are subsequently annealed (Ghosh S. et al., Nano Research, 2009, 2, pp. 183-191).

Lee et al. have recently used the reaction of diazoniums with SWNTs to suppress the conductivity of the metallic SWNTs and to use the unseparated mixture as source of semiconducting SWNTs for applications in electronics. They are CoMocat® SWNTs (having a small diameter, that is to say a diameter of between 0.7 and 0.9 nm) dissolved in an aqueous SDS solution. The selectivity with regard to the metallic SWNTs can be estimated, from the spectra, at approximately 3, that is to say that the speed of reaction of the metallic SWNTs is approximately 3 times greater than the speed of reaction of the semiconducting SWNTs (Lee C W. et al., Advanced Materials, 2010, 22, p. 1278).

It should be noted that, for all these methods, whether they are based on covalent coupling or complexing, the selectivity and consequently the separation are better when SWNTs having small diameters are concerned, that is to say a diameter of less than or equal to 1.1 nm (such as CoMocat or HiPco). If SWNTs having greater diameters are concerned, that is to say a diameter of greater than 1.1 nm, in particular a diameter of between 1.2 and 2 nm, limits included, such as the SWNTs obtained by electric arc, by laser or by CVD (chemical vapor deposition), the selectivity decreases. This is because it has been found that the physical and chemical properties are less marked when the diameter of the SWNTs increases; in particular, their reactivity has a tendency to decrease. Due to their better contact with the metal electrodes, semiconducting SWNTs having greater diameters are preferred for electronic devices (Zhang L et al., Journal of the American Chemical Society, 2008, 130, pp. 2686-2691).

Furthermore, during the reaction of diazoniums, in particular the aryldiazoniums, with the SWNTs, said aryldiazoniums prove to be selective toward metallic SWNTs but not specifically. In other words, the reaction does not make it possible to functionalize solely the metallic SWNTs and the diazoniums also react with the semiconducting SWNTs with a lower but not insignificant speed.

Application WO 2010089395 describes a process for the separation of SWNTs based on the reaction of a diazonium derivative, the diazoester, with the SWNTs in order to differentiate and separate the metallic SWNTs from the semiconducting SWNTs. This results in a covalent functionalization of the metallic SWNTs which is approximately 10 times greater than the functionalization of the semiconducting SWNTs. As the coupling suppresses the conductivity of the SWNTs, the metallic SWNTs can no longer produce a short circuit. The material can thus be used directly for applications in electronics, as recently demonstrated (Schmidt G. et al., Chemistry European Journal, 2011, 17, pp. 1415-1418). Once differentiated, the metallic SWNTs and the semiconducting SWNTs are separated from one another and then heat treated at 400° C. (Cabana J. et al., Journal of the American Chemical Society, 2007, 129, p. 2244) for more demanding applications, such as photonics. Despite a greater selectivity of this method in comparison with the methods already known, the separation of the SWNTs having large diameters as defined above remains difficult.

A complexing/adsorption method has recently been described in which the SWNTs, dissolved in an aqueous solution of SDS (sodium lauryl sulfate or sodium dodecyl sulfate), are separated by agarose gel chromatography (Tanaka T et al., Nano Letters, 2009, 9, pp. 1497-1500, and Moshammer K. et al., Nano Research, 2009, pp. 599-606). However, like the majority of separation methods, the separation is not perfect and the semiconducting SWNTs obtained still comprise a small fraction of highly conductive metallic SWNTs capable of producing short circuits in the electronic devices, for example.

Among all the methods for differentiating, enriching or separating SWNTs described in the literature, to date only the process for separation by ultracentrifuging over a density gradient has resulted in the commercialization of semiconducting SWNTs and metallic SWNTs in separated form (Arnold M S. et al., Nature Nanotechnology, 2006, 1, pp. 60-65). The semiconducting SWNTs and the metallic SWNTs separated according to this process are sold by Nanointegris at a price of $150/mg for a purity of 90% and $800/mg for a purity of 99%. Despite the high degree of purity advertized, 99% pure semiconducting SWNTs are not easy to use. For example, in a transistor channel using numerous SWNTs in parallel in order to bring about a fall in the overall resistance (approximately 6 k$\Omega$ by a carbon nanotube), a short circuit due to the presence of just one metallic single-walled carbon nanotube remains highly probable.

There thus remains a real need for a process which makes possible the differentiation of metallic SWNTs with respect to semiconducting SWNTs by a selective functionalization of said metallic SWNTs which overcomes the disadvantages of the prior art.

In particular, there exists a real need for a process which makes possible the functionalization of the metallic SWNTs, a significantly improved selectivity with respect to that described for the processes of the prior art, this being independently of the diameter of the SWNTs.

In addition, there exists a real need for a process which makes possible the functionalization of the SWNTs which can be carried out industrially.

SUMMARY

It is a specific aim of the present invention to meet these needs by providing a process for the selective functionalization of metallic single-walled carbon nanotubes, characterized in that, at pH<5:

an aqueous dispersion comprising a mixture of metallic single-walled carbon nanotubes and of semiconducting single-walled carbon nanotubes and a cationic surfactant is reacted, with an ascorbic (Z)-diazoester of formula (I):

in which:

$R^5$ and $R^6$, which are different, are chosen, independently of one another, from a hydrogen atom or an $R^1$—N=N— group;

$R^1$ represents a $C_{6-10}$ aryl group or a pyridyl group, said aryl and pyridyl groups optionally being substituted by one or more substituents chosen from a halogen atom chosen from chlorine or bromine, —$NO_2$, —$CO_2H$, —$CO_2R^3$, —$R^3$ or —$OR^3$;

$R^2$ and $R^4$, which are identical or different, are chosen, independently of one another, from a hydrogen atom or a $C_{1-20}$ alkyl group, —CO—($C_{1-20}$ alkyl), —$R^3$, —$CO_2R^3$, —CO—$NHR^3$ or —CO—$NR^3R^7$ group;

$R^3$ and $R^7$, which are identical or different, are chosen, independently of one another, from a $C_{1-20}$ alkyl group or a halo($C_{1-20}$ alkyl) group.

As indicated, $R^5$ is different from $R^6$. In other words, when $R^5$ represents a hydrogen atom, $R^6$ represents an $R^1$—N=N— group and, when $R^5$ represents an $R^1$—N=N— group, $R^6$ represents a hydrogen atom.

When the following three conditions are met, namely the use of a cationic surfactant, the pH<5 and the use of an ascorbic (Z)-diazoester as diazoester, a selectivity of 20 to 100 between the speed of coupling to the metallic SWNTs and to the semiconductors is obtained, both for the SWNTs having small diameters (that is to say, for the diameters of less than or equal to 1.1 nm) and for the SWNTs having large diameters (that is to say, for the diameters of greater than 1.1 nm).

Within the meaning of the invention, the term "ascorbic (Z)-diazoester" is understood to mean a compound of formula (I) in which the —N=N— double bond in the $R^1$—N=N— group is a Z configuration.

Within the meaning of the invention, the term "$C_{1-20}$ alkyl" group is understood to mean a saturated, optionally substituted, linear, branched or cyclic monovalent hydrocarbon group comprising from 1 to 20 carbon atoms. Mention may be made, by way of indication, of the methyl, ethyl, propyl, butyl, isobutyl, pentyl, hexyl, octyl, nonyl, decyl, undecyl, dodecyl, tridecyl, tetradecyl, pentadecyl, hexadecyl, heptadecyl, octadecyl, nonadecyl or eicosanyl groups and their branched isomers. Mention may also be made, as cyclic alkyl, of the cyclopropyl, cyclobutyl, cyclopentyl, cyclohexyl, bicyclo[2.1.1]hexyl or bicyclo[2.2.1]heptyl groups. The alkyl group can optionally be substituted by one or more hydroxyls, by one or more $C_{6-10}$ aryl group(s) as defined below or by one or more halogen atoms chosen from fluorine, chlorine, bromine or iodine. The alkyl group can, for example, comprise from 1 to 16 carbon atoms.

The term "halo($C_{1-20}$ alkyl)" means a $C_{1-20}$ alkyl group as defined above comprising at least one halogen atom chosen from fluorine, chlorine, bromine and/or iodine. Preferably, the halogen atom is a fluorine atom. Mention may be made, by way of example, of —$CF_3$, —$CH_2$—$CF_3$, —$C_2F_5$, —CH($CF_3$)$_2$, —CH($CH_3$)($CF_3$), —$C_3F_7$, —$C_4F_9$, —$C_5F_{11}$, —$C_6F_{13}$, —$C_7F_{15}$, —$C_8F_{17}$, —$C_9F_{19}$ or —$C_{10}F_{21}$.

The term "$C_{6-10}$ aryl" denotes generally a cyclic aromatic substituent comprising from 6 to 10 carbon atoms. In the context of the invention, the aryl group can be mono- or polycyclic. Mention may be made, by way of indication, of the phenyl and naphthyl groups. The aryl group can optionally be substituted by one or more substituents chosen from a halogen atom chosen from fluorine, chlorine, bromine or iodine; —$NO_2$; —$CO_2H$; —$CO_2R^3$, —$R^3$ or —$OR^3$, with $R^3$ being a $C_{1-20}$ alkyl group or a halo($C_{1-20}$ alkyl) group as defined above.

The term "pyridyl" denotes a heterocyclic aromatic substituent of formula $C_5H_5N$. The pyridyl group can optionally be substituted by one or more substituents chosen from a halogen atom chosen from fluorine, chlorine, bromine or iodine; —$NO_2$; —$CO_2H$; —$CO_2R^3$, —$R^3$ or —$OR^3$, with $R^3$ being a $C_{1-20}$ alkyl group or a halo($C_{1-20}$ alkyl) group as defined above.

The term "halogen" atom is understood to mean, in the context of the present invention, fluorine, chlorine, bromine or iodine.

The term "optionally substituted" is understood to mean a group in which one, two, three or more atoms can be replaced by one, two, three or more appropriate substituents, including, without limitation, a hydroxyl, a halogen atom, a $C_{6-10}$ aryl group as defined above; —$NO_2$; —$CO_2H$; —$CO_2R^3$, —$R^3$ or —$OR^3$, with $R^3$ being a $C_{1-20}$ alkyl group or a halo ($C_{1-20}$ alkyl) group as defined above.

The term "selectivity" within the meaning of the invention denotes the ratio of the rates of reaction of the reactant, in this case the ascorbic (Z)-diazoester of formula (I), with one type of carbon nanotubes, in this case the metallic SWNTs, to the rates of reaction of the reactant with the other type of carbon nanotubes, in this case the semiconducting SWNTs. A selective reaction can thus result in a mixture of products being obtained, one being predominant and the other being minor.

The term "specificity" within the meaning of the invention denotes a reaction in which the reactant, in this case the ascorbic (Z)-diazoester of formula (I), reacts only with a single type of single-walled carbon nanotubes. A reaction of infinite selectivity for one type of SWNTs is a reaction which is specific with regard to the same type of SWNTs.

In the context of the present invention, the term "dispersion" is understood to mean a suspension or dispersion of two separate phases: a dispersing medium (a solvent or a mixture of solvents) and a dispersed phase (the single-walled carbon nanotubes and the cationic surfactant, for example). The dispersion or suspension is "stable" when the dispersed phase (the single-walled nanotubes and the cationic surfactant, for example) do not sediment out. The dispersion is "homogeneous" when the phase dispersed in the dispersion medium is not visible to the naked eye or using an optical microscope. When the dispersion is homogeneous, it can also be regarded as a "solution". Thus, the term "dispersion" simultaneously encompasses dispersions, suspensions and solutions.

When at least one of the solvents of the dispersion medium is water, the dispersion or the solution is "aqueous".

Within the meaning of the invention, a buffer solution denotes a mixture composed of a weak acid (to provide protons to a strong acid) and its conjugate base (to capture the protons from a strong acid) or of a weak base (to capture the protons from a strong acid) and its conjugate acid (to transfer its protons to a strong base) and which makes it possible to keep the pH of a medium constant despite the addition of small amounts of an acid or base, or despite diluting.

Advantageously, the nanotubes employed in the context of the present invention are carbon nanotubes exhibiting:

a length of between 10 nm and 400 µm, in particular between 50 nm and 20 µm, more particularly between 200 nm and 2 µm, limits included, and a diameter of between 0.2 and 6 nm, in particular between 0.6 and 4 nm, more particularly between 0.7 and 2 nm, limits included.

Mention may be made, as examples of single-walled carbon nanotubes, of the CoMocat® or HiPco® SWNTs, the SWNTs obtained by laser synthesis (according to the synthesis described by O. Jost et al., Applied Physics Letters, 1999, 75, p. 2217), the SWNTs obtained by electric arc having the commercial source Nanoledge, Nanocarb® (Russia), Carbon Solutions (USA), or also the SWNTs obtained by CVD (Nanocyl).

The concentration of single-walled nanotubes (SWNT) in the aqueous dispersion can be between $1\times10^{-5}$ and 10 g/l, advantageously between $1\times10^{-4}$ and 1 g/l and more advantageously between $1\times10^{-3}$ and $1\times10^{-1}$ g/l, limits included.

The metallic SWNTs/semiconducting SWNTs ratio in the aqueous dispersion can vary as a function of the conditions used during the synthesis of these nanotubes.

Prior to the dispersion thereof and subsequent to the preparation thereof, the carbon nanotubes can be subjected to a treatment, in particular in order to remove the metal catalyst particles used during the preparation thereof and the carbon-based byproducts. Thus, any technique known to a person skilled in the art which makes such a treatment possible can be used in the context of the present invention.

Mention may be made, as example of treatment, of a treatment of the mixture of the metallic SWNTs and the semiconducting SWNTs with nitric acid and size exclusion chromatography of said mixture subsequent to said treatment. It is also possible to apply an ultrasound treatment before, during and/or after the exposure to nitric acid.

The dispersing of the mixture of metallic single-walled carbon nanotubes and semiconducting carbon nanotubes can be carried out by any means known to a person skilled in the art.

As indicated above, the use of surfactants with the SWNTs is already described. The surfactants conventionally used are anionic surfactants, such as SDS (sodium lauryl sulfate or sodium dodecyl sulfate), SDBS (4-dodecylbenzenesulfonic acid) or sodium cholate, and neutral surfactants, such as Triton X100 or poloxamers. In the process of the invention, the surfactant is cationic.

The cationic surfactants of the invention make it possible not only to modulate the reactivity of the SWNTs and of the diazoester but in addition to ensure optimum solubilization of the SWNTs.

In the process of the invention, the cationic surfactants employed are advantageously chosen from dodecyltrimethylammonium bromide, hexadecyltrimethylammonium bromide (referred to as CTAB), octadecyltrimethylammonium bromide, dodecyltrimethylammonium chloride, hexadecylpyridinium chloride, poly((4-vinylpyridine)-co-butyl methacrylate) or poly((4-vinylpyridine)-co-styrene). Preferably, the cationic surfactants are chosen from dodecyltrimethylammonium bromide, hexadecyltrimethylammonium bromide (referred to as CTAB), octadecyltrimethylammonium bromide, dodecyltrimethylammonium chloride or hexadecylpyridinium chloride.

The cationic surfactant can be introduced into the dispersion comprising the SWNTs as such or in solution in a polar solvent, preferably the same as that of the dispersion of the SWNTs.

The cationic surfactant in the aqueous dispersion is present preferably in an amount of between 0.001% and 10%, in particular between 0.01% and 5% and more particularly between 0.2% and 1%, limits included, by weight, with respect to the total weight of the dispersion.

The dispersion comprising the mixture of the nanotubes and the surfactant is aqueous, which means that it comprises at least water as solvent.

In addition to the water, said dispersion can comprise one or more other polar solvents, preferably polar protic solvents.

The term "polar protic solvent" is understood to mean a solvent that exhibits a dielectric constant of greater than 7, preferably of greater than 15, and which has one or more acidic hydrogens. Mention may be made, by way of indication, of water, methanol, ethanol, propanol, isopropanol, n-butanol or formic acid.

The reaction of the diazoniums of the state of the art with the SWNTs generally uses an aqueous medium but generally without control of the pH.

It has been found that, when, in the process of the invention, the pH of the dispersion is maintained at an acidic pH, in particular pH<5, the selectivity and the specificity of the functionalization of the metallic SWNTs by an ascorbic (Z)-diazoester of formula (I) is substantially improved.

Thus, the pH of the dispersion is more particularly greater than or equal to 0 and less than 5, preferably between 0.5 and 3.5 and more preferably between 1 and 2.5, limits included.

The pH of the dispersion can be kept constant by addition of a buffer solution. The buffer solution, when it is acidic, can be chosen, for example, from $CH_3CO_2H/CH_3CO_2^-$, $H_3PO_4/H_2PO_4^-$ or $C_6H_5CO_2H/C_6H_5CO_2^-$. The buffer solution, when it is basic, can be chosen, for example, from $NH_4^+/NH_3$, $(CH_3)_3NH^+/(CH_3)_3N$ or $H_2PO_4^-/HPO_4^{2-}$. Preferably, the pH of the dispersion is kept constant by addition of an acidic buffer solution. A person skilled in the art will know how to determine the amount of buffer solution to be employed in order to keep the pH of the dispersion at the desired pH values.

DETAILED DESCRIPTION

Figure 1:
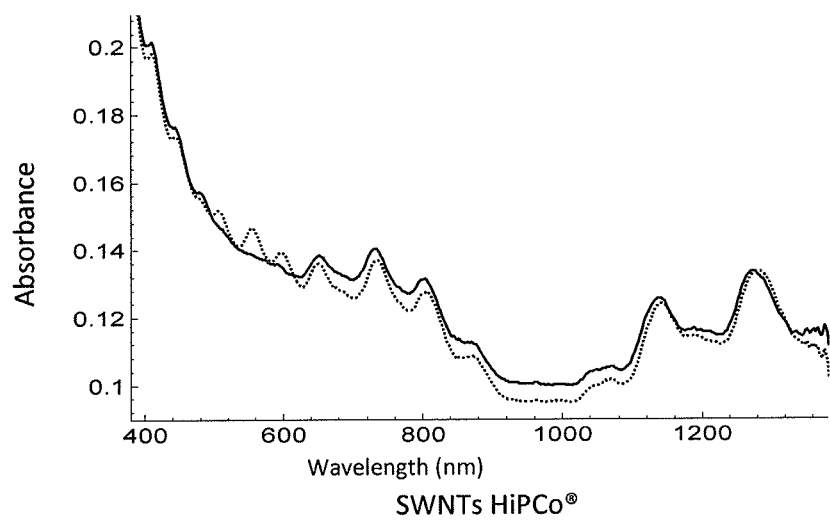
FIG. 1 represents an example of selective functionalization of the metallic SWNTs in a mixture of metallic SWNTs and semiconducting SWNTs CoMocat® and in a mixture of metallic SWNTs and semiconducting SWNTs HiPco®.
Figure 1:
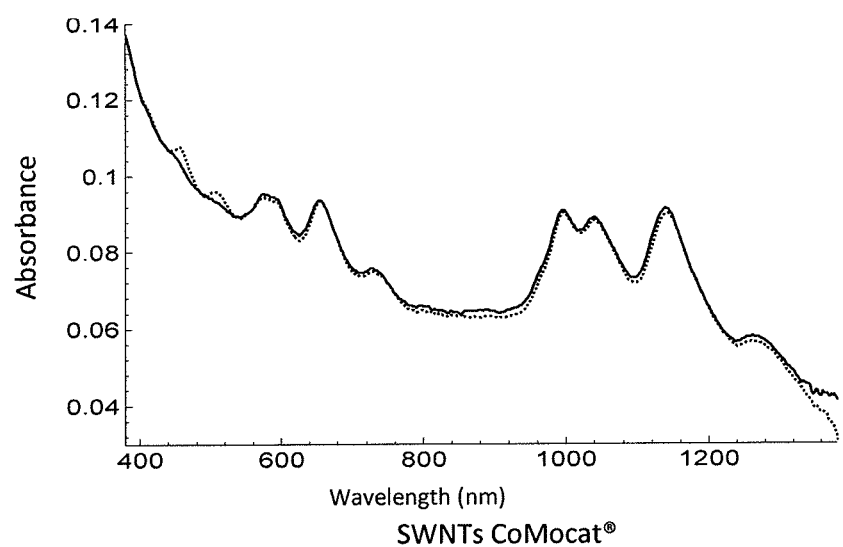

In the process of the invention, the ascorbic (Z)-diazoester of formula (I) can be obtained by reaction of a diazonium salt of formula (II) with a compound of formula (III):

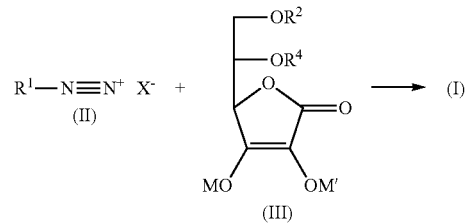

in which:

$R^1$, $R^2$ and $R^4$ are as defined above;

M and M', which are identical or different, are chosen, independently of one another, from a hydrogen atom or an alkali metal chosen from sodium or potassium;

$X^-$ represents a halogen atom chosen from fluorine, chlorine, bromine or iodine or an anion chosen from $BF_4^-$, $ClO_4^-$ or $SO_3^-$.

According to an alternative form of the invention, M is different from M'. In other words, when M represents a hydrogen atom, M' represents an alkali metal chosen from sodium or potassium and, when M represents an alkali metal chosen from sodium or potassium, M' represents a hydrogen atom.

Diazonium salts have been known for a long time to form esters (in some cases referred to as ethers) with oxygen-comprising compounds, first in the form of (Z)-diazoesters, which are rapidly converted into (E)-diazoesters by change in conformation. The ascorbic diazoester of (E) conformation is remarkably stable and is inactive with regard to coupling with SWNTs (Zollinger H, VCH, 1994, pp. 108-115; Doyle M P. et al., Journal of Organic Chemistry, 1989, 54, pp. 3785-3789; G. Schmidt et al., Chemistry—a European Journal, 2011, 17, p. 1415).

The process of the invention thus makes possible the reaction of the SWNTs with a diazoester of (Z) conformation, the reactivity of which has been adjusted in order to make possible a much greater selectivity than that described with the diazoniums or diazoesters of the state of the art.

Preferably, the diazonium salts of formula (II) are chosen from the group consisting of 4-nitrobenzenediazonium tetrafluoroborate, methyl 4-diazobenzoate tetrafluoroborate, 4-diazobenzoic acid tetrafluoroborate, 4-diazophthalic acid tetrafluoroborate and dimethyl 4-diazophthalate tetrafluoroborate.

It is particularly advantageous to use, as compounds of formula (III), a compound chosen from the group consisting of ascorbic acid, sodium ascorbate or sodium 6-O-palmitoy-lascorbate.

The ascorbic (Z)-diazoester of formula (I) can be prepared separately, before it is introduced into the aqueous dispersion comprising the SWNTs, by a process employing the stages consisting in:

a) preparing or taking an aqueous solution of the compound of formula (III);

b) introducing the diazonium salt of formula (II) as defined above into the solution obtained in stage a), c) introducing the solution resulting from stage b) into the aqueous dispersion comprising the SWNTs and the cationic surfactant.

It should be noted that, during the introduction of the solution resulting from stage b) into the aqueous dispersion of SWNTs, the pH of said aqueous dispersion is maintained at a pH<5.

As indicated, the solution of stage a) is an aqueous solution, meaning that the solvent is at least water. The water can optionally be a mixture with one or more "polar protic" solvent(s) as defined above. Preferably, the solvent(s) is (are) the same as that (those) of the dispersion. The solvent of stage a) is advantageously water.

The aqueous solution of stage a) can be prepared by mixing the compound of formula (III) with the solvent(s) with manual stirring.

The duration of stage b) can range from 1 second to 1 hour, for example from 3 seconds to 10 minutes and in particular from 5 seconds to 1 minute, limits included.

The solution resulting from stage b) is preferably immediately introduced into said dispersion. The term "immediately" is understood to mean as soon as the diazonium salt of formula (II) forms a homogeneous solution in which said salt is completely dissolved or, at the very least, appears to be completely dissolved to the naked eye or using an optical microscope.

Alternatively the ascorbic (Z)-diazoester of formula (I) can be prepared in situ by a process employing the stages consisting in:

i) introducing an aqueous solution of the compound of formula (III) into the dispersion comprising the SWNTs and the cationic surfactant; and ii) introducing an aqueous solution of the diazonium salt into the dispersion resulting from stage i).

During this process, the pH of said dispersion is maintained at pH<5.

In this alternative processing form, the operating conditions are the same as those of the preceding alternative form, in particular in terms of stirring means, reaction time and choice of solvent(s).

Whether the (Z)-diazoester of formula (I) is prepared separately or in situ, the molar ratio of the diazonium salt of formula (II) to the compound of formula (III) is from 0.001 to 1.5 and preferably from 0.01 to 1 molar equivalent, limits included.

Where the (Z)-diazoester of formula (I) is prepared separately or in situ, the contacting operation and thus the reaction between the diazonium salt of formula (II) and the compound of formula (III) is carried out at a temperature of between 0 and 50° C., for example between 1 and 40° C., limits included, advantageously at the temperature of the refrigerator, that is to say at a temperature of 4° C.±3° C.

According to a preferred alternative form of the invention, the (Z)-diazoester of formula (I) is prepared separately. Thus, stage b), that is to say the stage during which the compounds of formulae (II) and (III) are mixed, is carried out at 4° C.±3° C. in order to limit as much as possible the spontaneous isomerization of the (Z)-diazoester to give ascorbic (E)-diazoester. However, stage c), that is to say the stage during which the solution resulting from stage b) is added to the aqueous dispersion of SWNTs, is carried out at ambient temperature (20° C.±5° C.).

As indicated, the ascorbic (Z)-diazoester is spontaneously converted into ascorbic (E)-diazoester by a very rapid (Z)-(E) isomerization reaction. As the (E)-diazoester is unreactive with regard to the SWNTs, it is essential to control this isomerization reaction by a clever choice of reaction conditions.

In the process of the invention, the functionalization of the SWNTs is carried out with the (Z)-diazoester of formula (I), the concentration of which in the dispersion of the mixture of nanotubes is from $1\times10^{-9}$ to 1 mol/l, in particular from $1\times10^{-7}$ to $1\times10^{-2}$ mol/l, more particularly still from $1\times10^{-6}$ to $1\times10^{-4}$ mol/l.

In the process of the invention, the reaction of the ascorbic (Z)-diazoester of formula (I) with the dispersion of SWNTs takes place between 0 and 50° C., preferably between 20 and 40° C., limits included. More preferably, the reaction of the ascorbic (Z)-diazoester of formula (I) with the dispersion of SWNTs takes place at ambient temperature, that is to say at a temperature of 20° C.±5° C.

The duration of reaction between the dispersion comprising the SWNTs and the ascorbic (Z)-diazoester of formula (I) is between 5 minutes and 48 hours, in particular between 15 minutes and 3 hours, more particularly between 15 minutes and 1 hour, limits included.

During the preparation of the various dispersions and/or solutions employed in the context of the present invention, the latter are subjected to stirring. Mention may be made, as examples of stirring means, of manual stirring, treatment with ultrasound, mechanical stirring or a combination of such techniques. These techniques may require the application of a magnetic stirrer, of a magnetic bar, of an ultrasound bath or of a mechanical stirrer comprising shafts, paddles, propellers, and the like. A person skilled in the art will know how to choose the stirring means suited to each case.

It is possible to use the mixture obtained by the process of the invention as is. This is because, following the reaction of the ascorbic (Z)-diazoester of formula (I) with the mixture of metallic SWNTs and semiconducting SWNTs, the properties of the metallic SWNTs are very greatly modified by the reaction, whereas the semiconducting SWNTs are preserved by virtue of the highly selective nature of the process of the invention (the conjunction of the use of the ascorbic (Z)-diazoester of formula (I), of the cationic surfactant and of the pH<5). Consequently, the mixture of the metallic SWNTs thus functionalized and of semiconducting SWNTs can be regarded as a source of "pure" semiconducting SWNTs. Such a mixture can, for this reason, be used to prepare transistor channels, in particular in electronics, electron-accepting materials, in particular in photovoltaics, nonlinear infrared photon emitters or absorbers, current-conducting electrodes, flexible transparent electrodes, antistatic coatings, chemical detectors and solar cells.

The process according to the invention can be followed by a stage of separation of the functionalized metallic single-walled carbon nanotubes from the semiconducting single-walled carbon nanotubes.

The separation of the functionalized metallic SWNTs from the semiconducting SWNTs can be carried out by any separation technique known in this field, such as, for example, a separation technique based on chemical affinity, on filtration, on centrifuging, on electrophoresis and/or on chromatography.

The process described in Japanese patent application JP 2007 031238 can also be used to carry out such a separation.

In addition to the separation stage, the process of the invention can also comprise a stage of heat treatment of the separated nanotubes.

Thus, after their separation, the functionalized metallic SWNTs and/or the semiconducting SWNTs can be subjected to a stage of heat treatment. The heat treatment can be carried out under dry conditions, such as is described by Cabana J. et al., Journal of the American Chemical Society, 2007, 129, p. 2244 or by Ghosh S. et al., Nano Research, 2009, 2, pp. 183-191. The heat treatment can also be carried out in solution, as described by Dyke C. A. et al., Synlett, 2004, 1, pp. 155-160.

A subject matter of the present invention is a mixture of selectively functionalized metallic single-walled carbon nanotubes and semiconducting single-walled carbon nanotubes obtained by the process of the invention.

Another subject matter of the present invention is the use of a mixture of selectively functionalized metallic single-walled carbon nanotubes and semiconducting single-walled carbon nanotubes, obtained by the process of the invention, in the preparation of transistor channels, in particular in electronics, electron-accepting materials, in particular in photovoltaics, nonlinear infrared photon emitters or absorbers, current-conducting electrodes, flexible transparent electrodes, antistatic coatings, chemical detectors and solar cells.

The present invention also relates to the functionalized metallic single-walled carbon nanotubes obtained by the separation of the functionalized metallic single-walled carbon nanotubes from the semiconducting single-walled carbon nanotubes which are in the mixture obtained by the process of the invention as well as to the uses of said separated functionalized metallic single-walled carbon nanotubes in the preparation of current-conducting electrodes, flexible transparent electrodes, antistatic coatings, vias and interconnections in electronics, current-conducting cables and solar cells.

The invention also relates to the functionalized metallic single-walled carbon nanotubes, separated as indicated above and which have been subjected to a heat treatment, in the preparation of current-conducting electrodes, flexible transparent electrodes, antistatic coatings, vias and interconnections in electronics, current-conducting cables and solar cells.

The heat treatment of the functionalized metallic single-walled carbon nanotubes results in their defunctionalization. This treatment can occur, for example, at the end of the assembling of the system in which the functionalized metallic single-walled carbon nanotubes are used, for example in order to facilitate the positioning thereof or to protect them from damage in the processing stage.

The invention also relates to the semiconducting single-walled carbon nanotubes obtained during the stage of separation of the functionalized metallic single-walled carbon nanotubes from the semiconducting single-walled carbon nanotubes and to the uses of said separated semiconducting single-walled carbon nanotubes in the preparation of transistor channels, in particular in electronics, electron-accepting materials, in particular in photovoltaics, nonlinear infrared photon emitters or absorbers, current-conducting electrodes, flexible transparent electrodes, antistatic coatings, chemical detectors and solar cells.

The invention additionally relates to the semiconducting single-walled carbon nanotubes, separated as indicated above and which have been subjected to a heat treatment, in the preparation of nonlinear infrared photon emitters or absorbers.

An additional subject matter of the invention is a process for the preparation of transistor channels, in particular in electronics, electron-accepting materials, in particular in photovoltaics, nonlinear infrared photon emitters or absorbers, current-conducting electrodes, flexible transparent electrodes, antistatic coatings, chemical detectors, vias and interconnections in electronics, current-conducting cables and solar cells, characterized in that it employs the process for the selective functionalization of metallic single-walled carbon nanotubes according to the invention.

The present invention also relates to a process for the separation of metallic single-walled carbon nanotubes from semiconducting single-walled carbon nanotubes, comprising a stage of selective functionalization of the metallic single-walled carbon nanotubes according to the process of the invention.

Other advantages and characteristics of the present invention can also appear on reading the examples below, given by way of illustration, and the appended figures:

FIG. 1 represents an example of selective functionalization of the metallic SWNTs in a mixture of metallic SWNTs and semiconducting SWNTs CoMocat® and in a mixture of metallic SWNTs and semiconducting SWNTs HiPco®. The figure shows the corrected absorbance spectra, as a function of the wavelength in nm, of SWNTs in aqueous solution in CTAB at pH 2.1, before and after reaction with the (Z)-diazoester resulting from the reaction of ascorbic acid with 4-diazophthalic acid. The absorbance spectra of the mixture of the SWNTs before functionalization (dotted line) and after functionalization (solid line) are corrected in accordance with the formula $$\text{corrected absorbance} = (\text{absorbance} - A \times 1240/(\text{wavelength in nm}))/A,$$

where $A$ is a constant chosen as best as possible for each type of SWNT in order to better show the absorption peaks on a flat curve, according to a well known procedure. Thus, in order to obtain the corrected absorbance, the absorbance due to the background noise is subtracted from the total absorbance. The functionalization of the metallic SWNTs with the (Z)-diazoester brings about the suppression of the corresponding absorption peaks between 450 and 530 nm for the CoMocat® SWNTs and between 500 and 600 nm for the HiPco®

Figure 2:
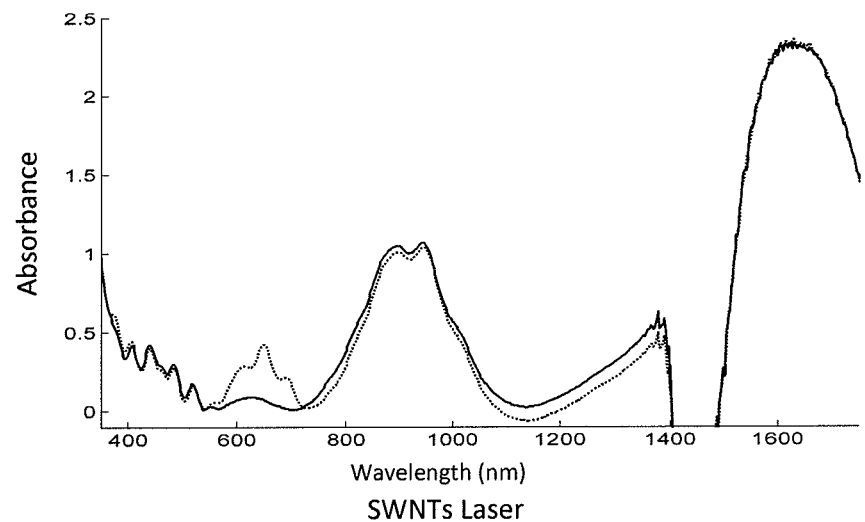
FIG. 2 represents an example of selective functionalization of the metallic SWNTs in a mixture of metallic SWNTs and semiconducting SWNTs obtained by laser, and in a mixture of metallic SWNTs and semiconducting SWNTs obtained by electric arc Nanoledge.
Figure 2:
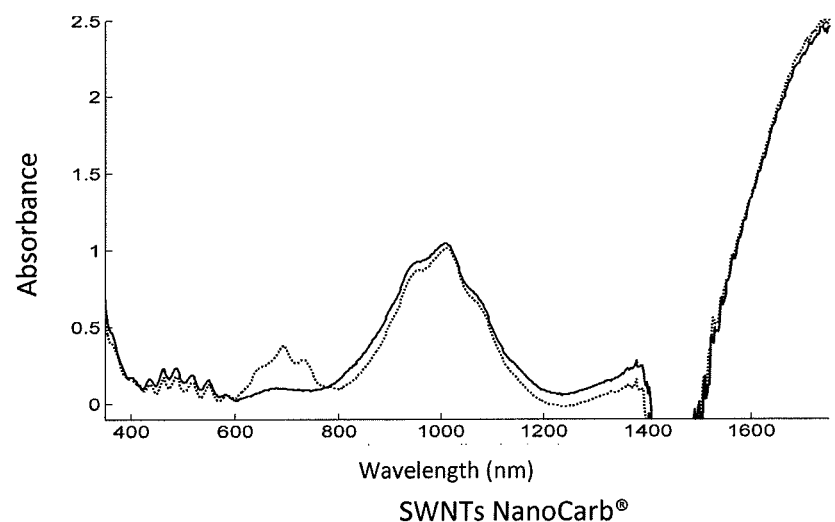
Figure 3:
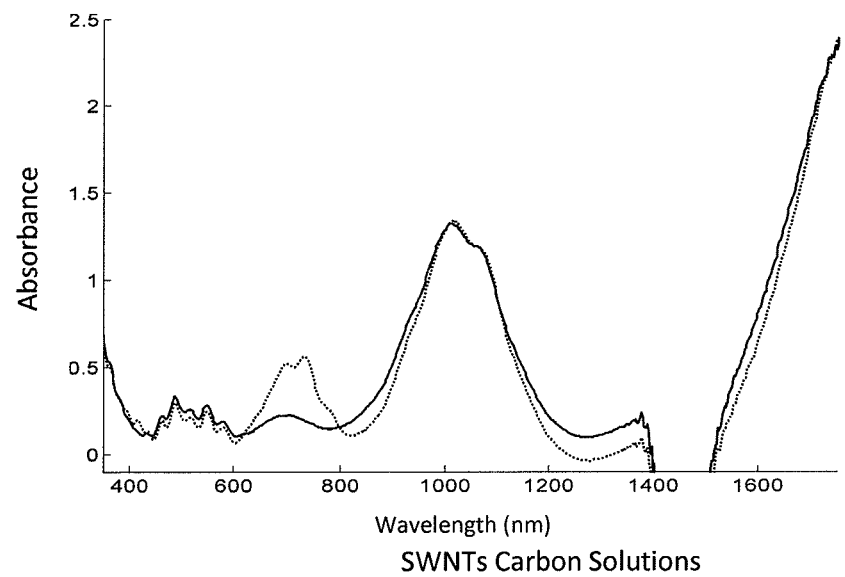
FIG. 3 represents an example of selective functionalization of the metallic SWNTs in a mixture of metallic SWNTs and semiconducting SWNTs obtained by electric arc Nano-Carb®, and in a mixture of metallic SWNTs and semiconducting SWNTs obtained by electric arc Carbon Solutions.
Figure 3:
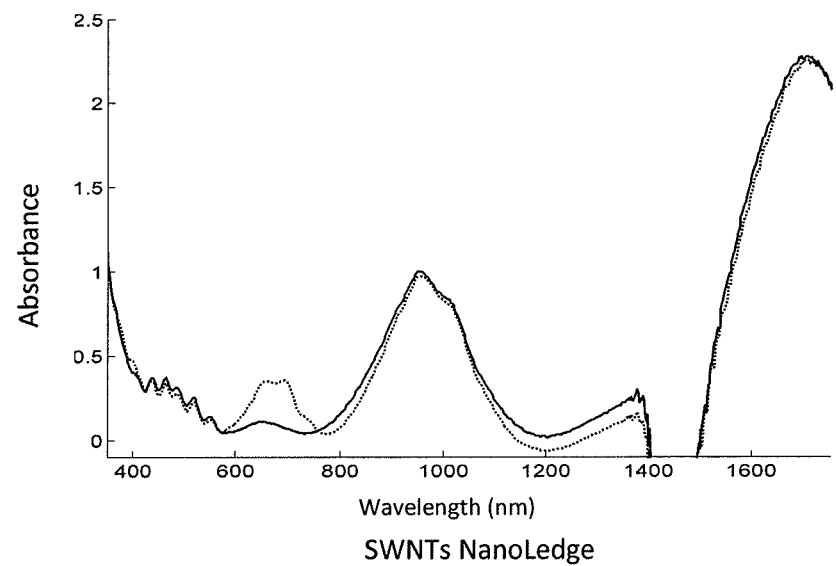
Figure 4:
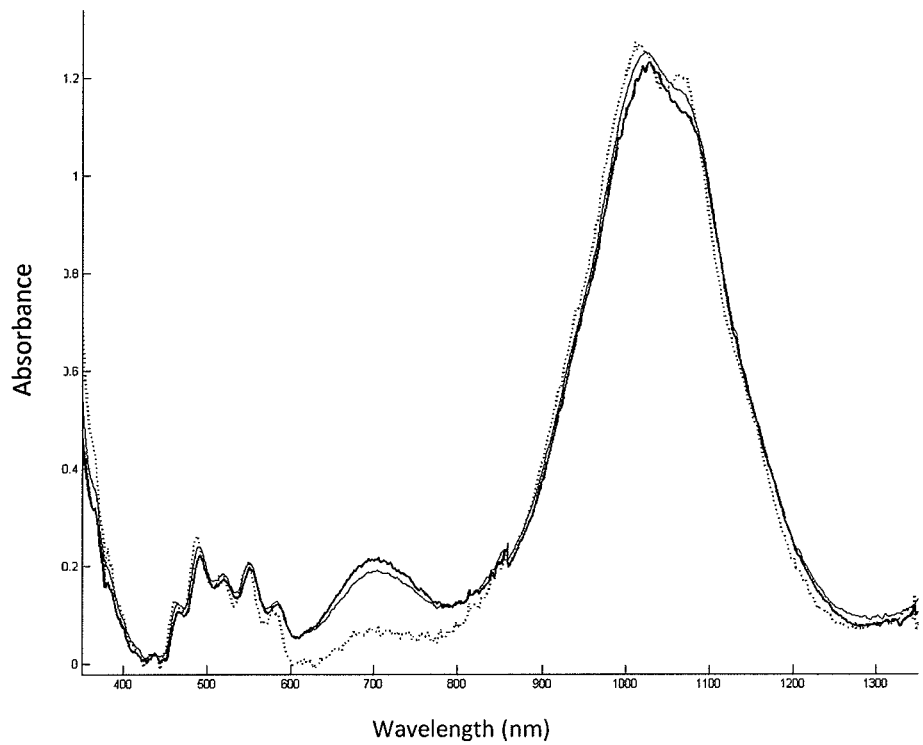
FIG. 4 represents the corrected absorbance spectra of a mixture of metallic SWNTs and semiconducting SWNTs of Carbon Solutions type as a function of the wavelength.

SWNTs, whereas the peaks of the semiconducting SWNTs at greater wavelength are not or only very slightly affected;

FIG. 2 represents an example of selective functionalization of the metallic SWNTs in a mixture of metallic SWNTs and semiconducting SWNTs obtained by laser (according to O. Jost et al., Applied Physics Letters, 1999, 75, p. 2217) and in a mixture of metallic SWNTs and semiconducting SWNTs obtained by electric arc Nanoledge. The figure shows the corrected absorbance spectra, as a function of the wavelength in nm, of SWNTs in aqueous solution in CTAB at pH 2.1, before and after reaction with the (Z)-diazoester resulting from the reaction of ascorbic acid with 4-diazophthalic acid. The absorption spectra of the mixture of SWNTs before functionalization (dotted line) and after functionalization (solid line) are corrected according to the corrected absorbance formula described for FIG. 1. In both types of mixture of SWNTs, laser and Nanoledge, the functionalization of the metallic SWNTs with the (Z)-diazoester results in the suppression of the corresponding absorption peaks between 600 and 800 nm whereas the peaks of the semiconducting SWNTs at greater wavelength are not or only very slightly affected;

FIG. 3 represents an example of selective functionalization of the metallic SWNTs in a mixture of metallic SWNTs and semiconducting SWNTs obtained by electric arc NanoCarb®, and in a mixture of metallic SWNTs and semiconducting SWNTs obtained by electric arc Carbon Solutions. The figure shows the corrected absorbance spectra, as a function of the wavelength in nm, of SWNTs in aqueous solution in CTAB at pH 2.1 before and after reaction with the (Z)-diazoester resulting from the reaction of ascorbic acid with 4-diazophthalic acid. The absorption spectra of the SWNTs before functionalization (dotted line) and after functionalization (solid line) are corrected according to the corrected absorbance formula described for FIG. 1. In both types of mixture of SWNTs NanoCarb® and Carbon Solutions, the functionalization of the metallic SWNTs with the (Z)-diazoester brings about the suppression of the corresponding absorption peaks between 600 and 800 nm whereas the peaks of the semiconducting SWNTs at greater wavelength are not or only very slightly affected;

FIG. 4 represents the corrected absorbance spectra of a mixture of metallic SWNTs and semiconducting SWNTs of Carbon Solutions type as a function of the wavelength. For a better comparison, the spectra are restandardized according to the formula Corrected absorbance=(absorbance−$A$×1240/(wavelength in nm))/$A$ where $A$ is the absorbance at 1240 nm. The absorption peaks of the semiconducting SWNTs appear between 900 and 1200 nm and between 400 and 600 nm, whereas the absorption peaks of the metallic SWNTs are visible between 600 and 800 nm. The curve as a thin gray line shows the spectrum of the solution of the mixture of SWNTs after functionalization and before separation. The curve as a dotted line shows the spectrum of the supernatant after centrifuging, with a considerably reduced peak for metallic SWNTs and slightly enhanced peaks for semiconducting SWNTs. The curve as a thick black line shows the spectrum of the centrifuging pellets resuspended in water with, on the other hand, an enhanced peak for metallic SWNTs and slightly reduced peaks for semiconducting SWNTs.

EXAMPLES

Example

Preparation of the Dispersion of the Mixture of Metallic Single-Walled Carbon Nanotubes and Semiconducting Single-Walled Carbon Nanotubes The mixture of metallic SWNTs and semiconducting SWNTs is weighed and mixed in a glass flask with a CTAB solution, typically 20 mg of SWNTs in 20 ml of solution of CTAB at 0.2% by weight with respect to the total weight of the dispersion.

The combination is subjected to ultrasound in order to form a homogeneous dispersion. Typically, use is made of an ultrasonic probe dipped into the solution at a power of 15 W for 15 minutes. The dispersion/solution is subsequently centrifuged in order to remove the metal catalysts residues, the amorphous carbon particles and the poorly dispersed carbon nanotubes, typically at 100 000 g for 30 minutes at 25° C. The supernatant is withdrawn and used as solution of SWNTs.

Functionalization of the Metallic Single-Walled Carbon Nanotubes by Coupling with the Ascorbic (Z)-Diazoester The dispersion/solution of the mixture of SWNTs obtained above is buffered to pH 2.1 by addition of a phosphate buffer. Typically, 100 µl of 0.5M $H_3PO_4$+0.5M $KH_2PO_4$ solution are added to 1 ml of solution of SWNTs.

A 10 mM solution of ascorbic acid in water is prepared at the time of use. A few milligrams of diazonium salt, typically 4-nitrobenzenediazonium tetrafluoroborate or 4-diazophthalic acid tetrafluoroborate, are weighed out. The diazonium salt is dissolved at 10 mM in the ascorbic acid solution and the mixture is immediately added with stirring to the solution of SWNTs in a proportion typically of 10 µl of this mixture per 1 ml of buffer solution of SWNTs.

Alternatively, the ascorbic acid can be added directly to the solution of SWNTs, typically in a proportion of 10 µl of 10 mM ascorbic acid in water per 1 ml of solution of SWNTs. The diazonium is dissolved at 1 mM in water. This solution is subsequently added to the solution of SWNTs, typically in a proportion of 100 µl of 1 mM diazonium solution per 1 ml of solution of SWNTs.

The critical points are the good dispersion/dissolution of the mixture of SWNTs, the use of a cationic surfactant, the acidic pH, the equimolar mixture of ascorbic acid and diazonium salt, and the rapid contact of the mixture with the dispersion/solution of SWNTs.

The ultracentrifuging conditions are either an ultrasonic treatment in an ultrasonic bath having a power of 80 W, 45 kHz, at full power, for 30 minutes to 2 hours, or an ultrasonic treatment with an ultrasonic probe dipped into the solution at a power of 15 W for 15 minutes to 2 hours.

The centrifuging conditions are: a duration of 30 minutes at a temperature of 10 to 25° C. with an acceleration of 80 000 to 120 000 g.

It has been found that, when the three following conditions are met, namely the use of a cationic surfactant, an acidic pH and the use of the ascorbic (Z)-diazoester of formula (I), the functionalization of the metallic SWNTs is highly selective (the semiconducting SWNTs are only very slightly or not at all affected by the coupling reaction), this being the case both for the SWNTs having small diameters HiPco and CoMocat (that is to say, for diameters of less than 1 nm) and for the SWNTs having large diameters obtained by laser and electric arc (Nanoledge, NanoCarb, Carbon Solutions, that is to say, for diameters of greater than 1 nm).

Separation of the Functionalized Metallic Single-Walled Carbon Nanotubes from the Nonfunctionalized Semiconducting Single-Walled Carbon Nanotubes After the functionalization of the metallic single-walled carbon nanotubes by the ascorbic ester of 4-diazophthalic acid, the reaction medium is centrifuged at 4° C. at a speed of 60 000 to 100 000 g for 45 minutes. The supernatant withdrawn is enriched in semiconducting SWNTs and depleted in functionalized metallic SWNTs.

FIG. 4 shows the corrected absorbance spectra for SWNTs of Carbon Solutions type as a function of the wavelength. The absorption peaks of the semiconducting SWNTs appear between 900 and 1200 nm and between 400 and 600 nm, whereas the absorption peaks of the metallic SWNTs are visible between 600 and 800 nm. The curve as a thin gray line shows the spectrum of the solution of SWNTs after differentiation and before separation. The curve as a dotted line shows the spectrum of the supernatant after centrifuging, with a considerably reduced peak for metallic SWNTs and slightly enhanced peaks for semiconducting SWNTs. The curve as a thick black line shows the spectrum of the centrifuging pellets resuspended in water with, on the other hand, an enhanced peak for metallic SWNTs and slightly reduced peaks for semiconducting SWNTs.

The invention claimed is:

1. A process for the selective functionalization of metallic single-walled carbon nanotubes, wherein at pH<5:
   an aqueous dispersion comprising a mixture of metallic single-walled carbon nanotubes and of semiconducting single-walled carbon nanotubes and a cationic surfactant is reacted, with
   an ascorbic (Z)-diazoester of formula (I):

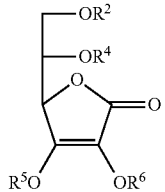

(I)

in which:
$R^5$ is an $R^1$—N=N— group;
$R^1$ represents a $C_{6\text{-}10}$ aryl group or a pyridyl group, said aryl and pyridyl groups optionally being substituted by one or more substituents chosen from a halogen atom chosen from chlorine or bromine, —$NO_2$, —$CO_2H$, —$CO_2R^3$, —$R^3$ or —$OR^3$;
$R^6$, $R^2$, and $R^4$ are a hydrogen atom
$R^3$ is a $C_{1\text{-}20}$ alkyl group or a halo($C_{1\text{-}20}$ alkyl) group.

2. The process as claimed in claim 1, wherein the metallic and semiconducting single-walled carbon nanotubes exhibit a length of between 10 nm and 400 μm, limits included, and a diameter of between 0.2 and 6 nm, limits included.

3. The process as claimed in claim 1, wherein the concentration of single-walled nanotubes in the aqueous dispersion is between $1\times10^{-5}$ and 10 g/l, limits included.

4. The process as claimed in claim 1, wherein the cationic surfactant is selected from the group consisting of dodecyltrimethylammonium bromide, hexadecyltrimethylammonium bromide, octadecyltrimethylammonium bromide, dodecyltrimethylammonium chloride, hexadecylpyridinium chloride, poly((4-vinylpyridine)-co-butyl methacrylate) and poly((4-vinylpyridine)-co-styrene).

5. The process as claimed in claim 1, wherein the cationic surfactant in the aqueous dispersion is present in an amount of between 0.001% and 10%, limits included, by weight, with respect to the total weight of the dispersion.

6. The process as claimed in claim 1, characterized in that wherein the pH is greater than or equal to 0 and less than 5.

7. The process as claimed in claim 1, wherein the pH is kept constant by addition of an acidic buffer solution selected from the group consisting of $CH_3CO_2H/CH_3CO_2^-$, $H_3PO_4/H_2PO_4^-$ and $C_6H_5CO_2H/C_6H_5CO_2^-$.

8. The process as claimed in claim 1, wherein the concentration of ascorbic (Z)-diazoester of formula (I) in the dispersion is from $1\times10^{-9}$ to 1 mol/l.

9. The process as claimed in claim 1, wherein the process is carried out at a temperature of between 0 and 50° C., limits included.

10. The process as claimed in claim 1, wherein the duration of reaction between said dispersion and the ascorbic (Z)-diazoester of formula (I) is between 5 minutes and 48 hours, limits included.

11. The process as claimed in claim 1, wherein the ascorbic (Z)-diazoester of formula (I) is obtained by reaction of a diazonium salt of formula (II) with an ascorbic acid compound of formula (III):

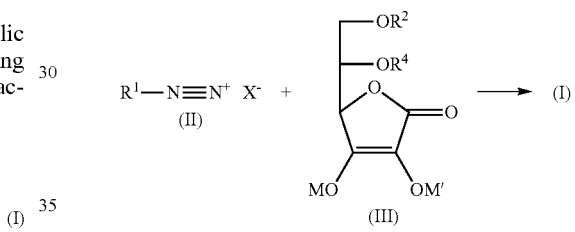

in which:
$R^1$, $R^2$, and $R^4$ are as defined in claim 1;
M and M', which are identical or different, are chosen, independently of one another, from a hydrogen atom or an alkali metal chosen from sodium or potassium;
$X^-$ represents a halogen atom chosen from fluorine, chlorine, bromine or iodine or an anion chosen from $BF_4^-$, $ClO_4^-$ or $SO_3^-$.

12. The process as claimed in claim 1, wherein the process is followed by a stage of separation of the functionalized metallic single-walled carbon nanotubes from the semiconducting single-walled carbon nanotubes.

13. The process as claimed in claim 12, wherein the process additionally comprises a stage of heat treatment of said nanotubes.

14. A method of preparing transistor channels, electron-accepting materials, nonlinear infrared photon emitters or absorbers, current-conducting electrodes, flexible transparent electrodes, antistatic coatings, chemical detectors and solar cells, the method comprising a step of selectively functionalizing of metallic single-walled carbon nanotubes according to the process of claim 1.

15. The functionalized metallic single-walled carbon nanotube obtained by the process as claimed in claim 12.

16. A method of preparing current-conducting electrodes, flexible transparent electrodes, antistatic coatings, vias and interconnections in electronics, current-conducting cables and solar cells, the method comprising a step of selectively functionalizing of metallic single-walled carbon nanotubes according to the process of claim 1.

17. A process for the separation of metallic single-walled carbon nanotubes from semiconducting single-walled carbon nanotubes, comprising a stage of selective functionalization of the metallic single-walled carbon nanotubes according to the process described in claim 1.

* * * * *

UNITED STATES PATENT AND TRADEMARK OFFICE
CERTIFICATE OF CORRECTION

PATENT NO. : 8,841,465 B2  
APPLICATION NO. : 14/124759  
DATED : September 23, 2014  
INVENTOR(S) : Chenevier Page 1 of 1

It is certified that error appears in the above-identified patent and that said Letters Patent is hereby corrected as shown below:

In the claims:

Column 16, Claim 6,
Line 5, cancel "characterized in that".

Signed and Sealed this
Twenty-first Day of April, 2015

Michelle K. Lee
*Director of the United States Patent and Trademark Office*